United States Patent [19]

Thompson

[11] 4,284,890
[45] Aug. 18, 1981

[54] COINCIDENCE ANALYSIS CIRCUIT FOR POSITRON ANNIHILATION IMAGING DEVICE

[75] Inventor: Christopher J. Thompson, Montreal, Canada

[73] Assignee: Montreal Neurological Institute, Montreal, Canada

[21] Appl. No.: 70,066

[22] Filed: Aug. 27, 1979

[51] Int. Cl.³ .................... G01T 1/20; G01N 21/00
[52] U.S. Cl. ................. 250/363 S; 250/366; 250/445 T
[58] Field of Search ............. 250/361 R, 363 S, 366, 250/369, 445 T

[56] References Cited

U.S. PATENT DOCUMENTS 4,181,855  1/1980  Horrocks .................... 250/366

OTHER PUBLICATIONS

Muehllehner, G. et al., "Performance Parameters of a Positron Imaging Camera", IEEE Transactions on Nuclear Science, vol. NS-23, No. 1, Feb. 1976, pp. 528–537.

Primary Examiner—Davis L. Willis
Assistant Examiner—Janice A. Howell
Attorney, Agent, or Firm—Beveridge, DeGrandi, Kline & Lunsford

[57] ABSTRACT

Apparatus for determining the instantaneous occurrence of coincident pulsed signals within a selected sampling time, which apparatus stores the coincident events and which provides the required algorithmic transformation necessary to determine coincident event distribution and an interface for the utilization of a general purpose computer.

1 Claim, 5 Drawing Figures

COINCIDENCE ANALYSIS CIRCUIT FOR POSITRON ANNIHILATION IMAGING DEVICE

BACKGROUND OF THE INVENTION

1. Field of the Invention

This invention relates generally to positron emission tomography and more particularly to devices which use an array of scintillation detectors to detect the annihilation radiation from positron disintegration and use this information to reconstruct an image of the distribution of positron emitting isotopes within a body.

2. Description of the Prior Art

Positron emission tomography is a technique for measuring the concentration of a positron emitting isotope through a sectional plane through the body. Normally the isotope is used to label a substance which circulates with the blood and which may be adsorbed in certain tissues. The technique allows the actual concentration in the slice to be determined if the device is suitably calibrated.

Certain isotopes decay by emitting a positively charged particle with the same mass as the electron (positron) and the neutrino from the nucleus. In this process one of the protons in the nucleus becomes a neutron, so that its atomic number goes down while its atomic weight remains constant. This positron is ejected with a kinetic energy of up to 2 MeV depending on the isotope and loses this energy by collisions while travelling a distance of up to a few mms in water. When it has reached thermal energies it interacts with an electron and they mutually annihilate one another. The rest mass of the 2 particles is transformed into 2 gamma rays of 511 KeV which are emitted at 180° in the 'center of mass' coordinates of the original particles. The 2 gamma rays may be detected by suitable devices. If these devices measure the energy of the gamma rays at 511 KeV and register this energy almost simultaneously it may be assumed that the origin of the radiation is on a straight line between the 2 detectors. Several detectors may be used in an arrangement so that many coincident events may be imaged during the same time interval. Then the information from these detectors is processed by a computer using image reconstruction techniques in order to find the location of distribution of positron emitting isotope.

COMPONENTS OF IMAGING DEVICE

A device for imaging positron annihilation radiation consists of the following basic parts:

(1) A number of detectors arranged in a precise geometrical pattern. These detectors are normally scintillation detectors in one or several planes, and these detectors are normally arranged in a polygonal pattern or around the circumference of a circle. Scintillation detectors emit a light flash each time they absorb gamma radiation which may or may not arise from the mutual annihilation of a positron and electron. The intensity of the light flash is proportional to the gamma ray energy.

(2) The device must contain a means of converting the light flash to an electrical charge pulse. Its amplitude is proportional to the light intensity.

(3) The device must contain a means of determining that the charge pulse could have arisen from a gamma ray whose energy was approximately equivalent to the mass of the electron at rest (511 KeV).

(4) The device must have an electric circuit capable of determining that 2 and only 2 of the detectors each recorded gamma rays of appropriate energy within a short time interval (coincidence resolving time). These detectors are said to have recorded a 'coincident event'.

(5) The device must have an electric circuit which determines which 2 detectors out of the many possible combinations recorded the so-called 'coincident event'.

(6) The device must have a memory in which it can record how often each pair of detectors record a 'coincident event'. The memory may be part of the random access memory of a general purpose computer.

(7) The device is required to use an algorithm through which the information in the memory may be transformed into an image of the distribution of positron annihilation per unit time in a cross-section surrounded by the detectors. The sequence of steps described by this algorithm may be programmed into a general purpose computer.

OBJECTS AND SUMMARY OF THE INVENTION

Accordingly it is the object of this invention to provide the means for determining if any two of the detectors recorded an event simultaneously.

It is the second object of this invention to provide a way of encoding the detector numbers in a unique way and to transmit this information to a memory where it can be used in reconstructing an image of the distribution of positron emitting isotope in a cross-section of the body being imaged.

A further object of this invention is to make a determination of the fact that only two events occurred and which detectors were involved in recording these events as quickly as possible to reduce the dead time of the coincidence circuit to a minimum.

A further object of this invention is to use only readily available commercial integrated circuits which do not require special programming techniques in order to generate the address.

A further object of this invention is to use an encoding scheme which allows the recording of coincidences between events which correspond to a pair of detectors the line joining which does not pass through the object being scanned. These detectors can only be involved in "random" or "scattered coincident events". This information can be used in the image reconstruction technique for measuring the scattered and random coincidences for detectors in which the line joining them does go through the object being scanned thus allowing corrections to be made for these unwanted events.

DESCRIPTION OF A PREFERRED EMBODIMENT

Figure 1:
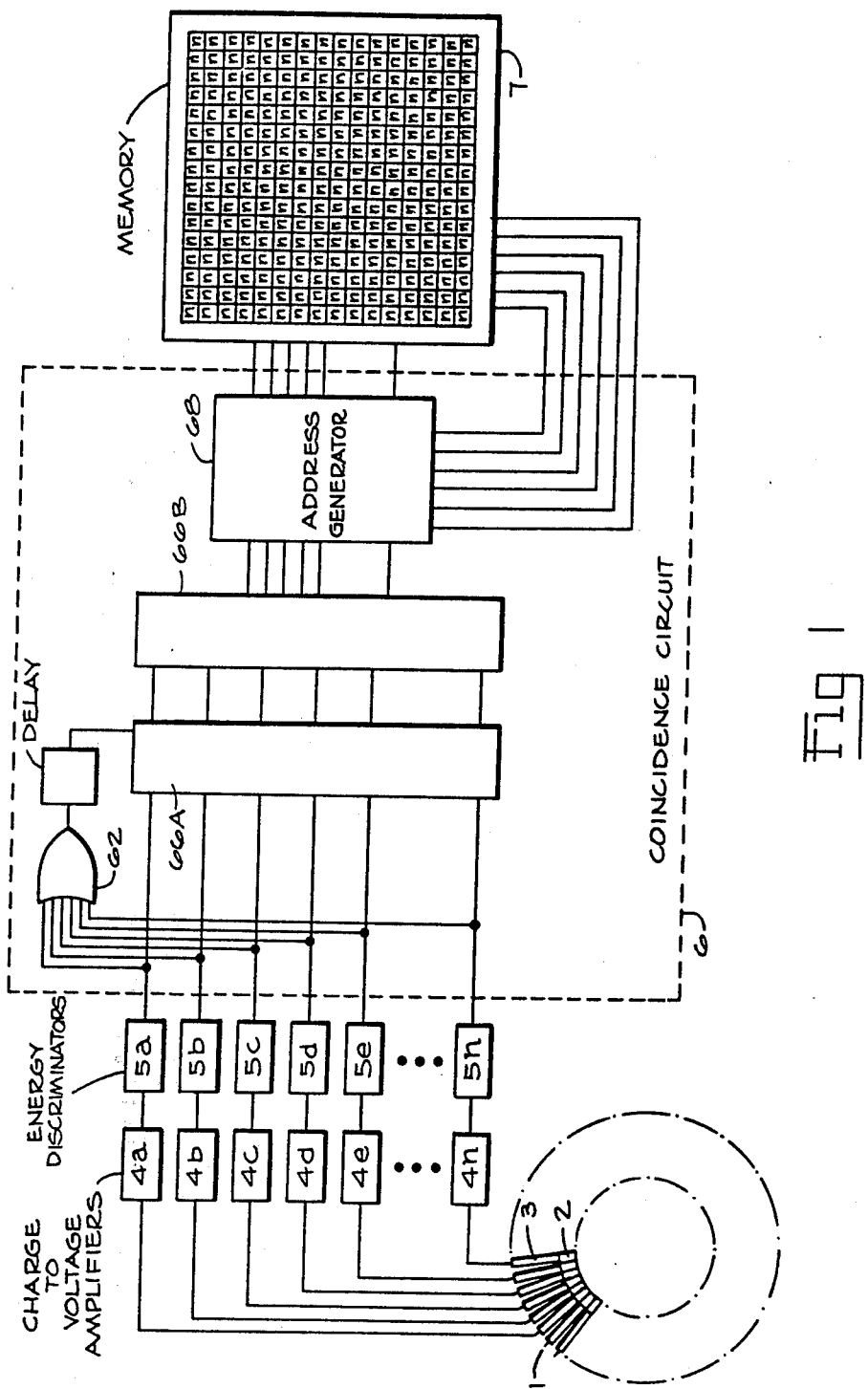
FIG. 1 is an overall block diagram of the apparatus.

The preferred embodiment of this positron annihilation imaging device 1 is shown in outlined form in FIG. 1. It is seen that the device consists of one or more rings of detectors 2 which surround the object being imaged in one or more planes. The light input from the detectors activates associated photo-multipliers 3. The electrical signals from these detectors are amplified at 4a, 4b–4n and their signal levels descriminated at 5a, 5b–5n, and the outputs of each of the energy discriminators are processed by the coincidence analysis circuit 6 which is the subject of this invention. The purpose of the coincidence analysis circuit 6 is primarily two fold: its first job is to determine if two or more detectors record a simultaneous event. If exactly two detectors record a simultaneous event, the coincidence analysis circuit 6 calculates the address of those two detectors and having found that address, in a memory to which it is attached, it increments that memory location. The information in the memory is subsequently processed by an image reconstruction program which, at the time of processing, has available to it the number of times a coincident event occurred between all possible combinations of detectors within the array.

Figure 2:
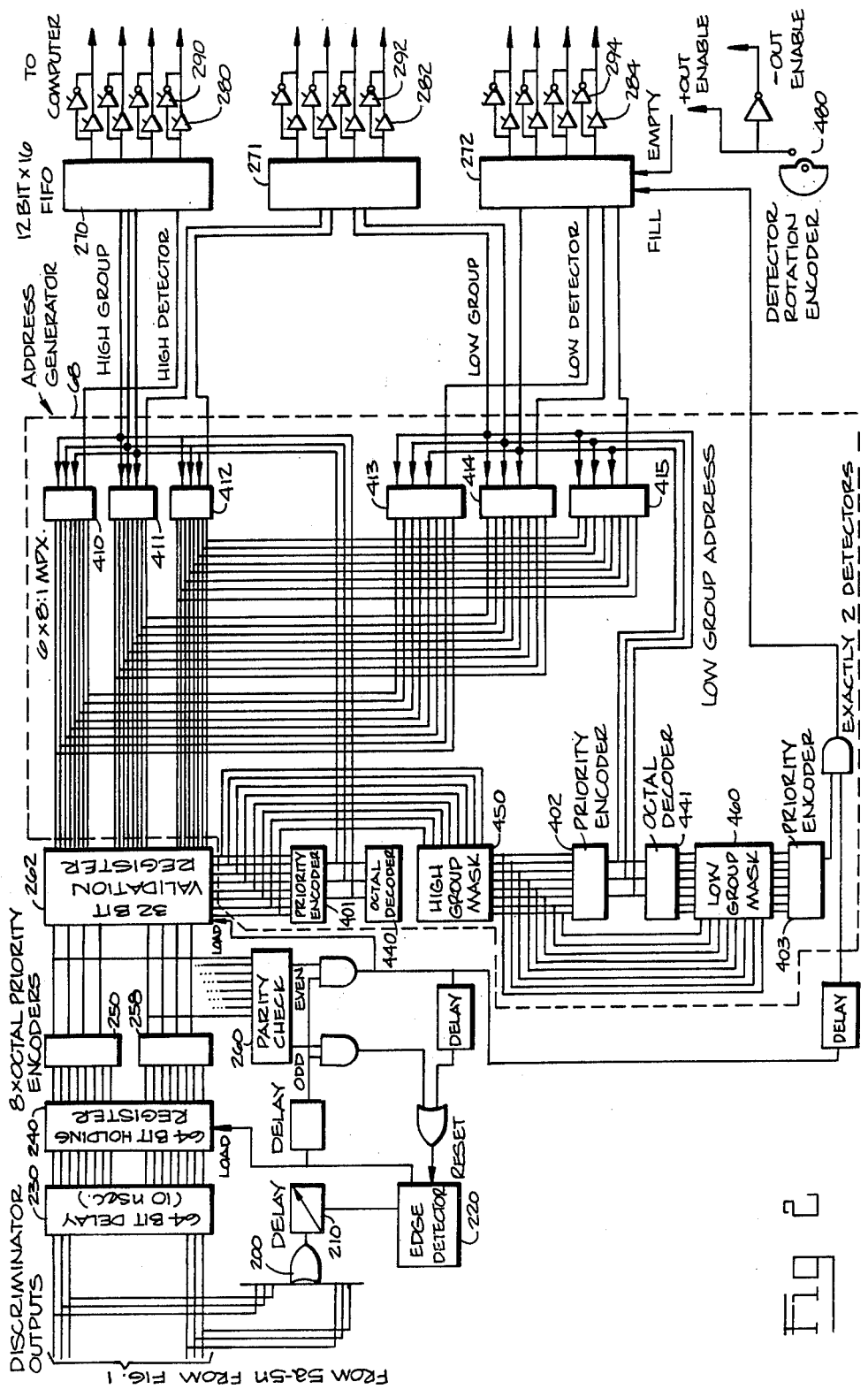
FIG. 2 is a block diagram of the coincidence analysis circuit.

Referring now to FIG. 2 which is a block diagram of the coincidence analysis circuit in more detail. The basic flow of information in this diagram is from left to right starting with 64 discriminator outputs and terminating with the 12 bit address which is sent to the computer's memory. The preferred embodiment contains rings of 64 detectors and the outputs of the detectors are connected to the discriminators 5a–5n in FIG. 1. The discriminators are triggered every time one of the detectors records an event which is within the desired energy range and the output of the discriminators are routed into a 64 input OR-gate 200 and a 64 bit delay 230. The output of the OR-gate 200 will be true whenever one of the 64 detectors records an event. The output of the OR-gate is delayed by a delay 210 and it triggers a D type flipflop 220 (edge detector) in the block diagram, the output of which is used to load a 64 bit holding register 240. The 64 bit delay register 330 and the delays 210 associated with the propagation of the signals through the OR-gate and the edge detector 220 determine the coincidence resolving time. The resolving time can be varied (210) in units of 3 nsec (the gate propagation delay for the circuits used). The delay register consists of 64 inverters with a significant propagation delay (10 nsec) compared with Schotlky TTL logic used in the rest of the circuit. That is, the time during which two detectors may be said to have recorded each of the two gamma rays from a positron anhilation. The output of the 64 bit holding register 240 is just the state of the detectors approximately 15 nsec (this is an adjustable coincidence resolving time) after the first detector recorded an event.

8 octal priority encoders 250/258 are connected to the output of this holding register. There are 8 input lines to each priority encoder and 4 output lines. Three of the outputs contain octal address of the most significant input line. The forth output line is true whenever one or more of the inputs is true. This fourth output of each priority encoder is input to a parity checking circuit 260 whose function is to determine whether an odd or an even number of detectors are involved in this event. This can be done extremely quickly. Since most of the time (approximately 90–98% of the time) only one detector is involved, this stage eliminates most of the information which requires no further processing. When the parity of the input event is seen to be even the 32 outputs of the 8 priority encoders are stored in a 32 bit validation register 262. The purpose of the validation register is to retain even parity events until the address generator can determine exactly which two detectors were involved in this particular event.

Figure 3:
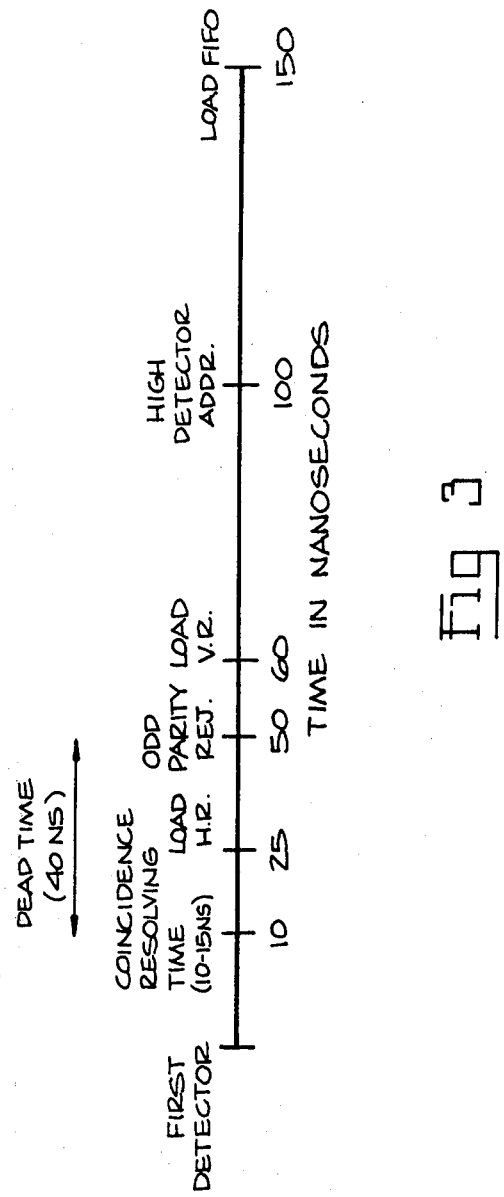
FIG. 3 is a timing diagram for the coincidence analysis circuit.

Referring briefly to the timing diagram if FIG. 3, it is seen that the "deadtime" of the 64 bit holding register circuit is only about 50 nsec. This implies that the circuit can process about one million events a second with a "deadtime" of only 5%. It can, of course, handle many more events per second than this at a proportionately higher deadtime.

Figure 4:
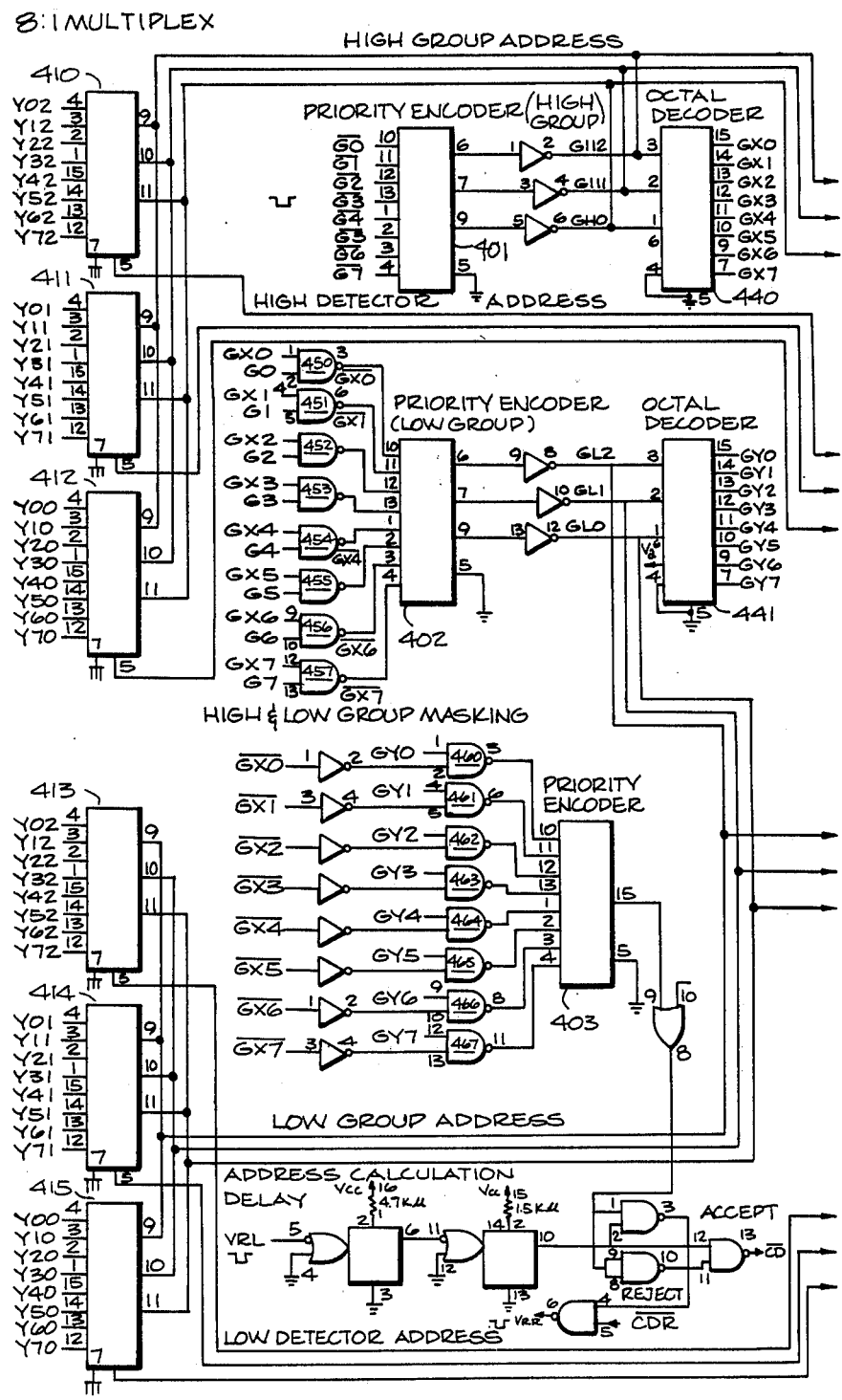
FIG. 4 is a detailed diagram showing the individual components of the address generator which is enclosed in dashed lines within FIG. 2, and, FIG. 5 is a black and white representation of the "raw data" from a real patient scan.

The key aspect of this invention is the address generator 68 which determines which two detectors are involved in a particular event. The block diagram of the address generator 68 is enclosed in the dotted line in FIG. 2 and the actual components used are shown in circuit diagram form in FIG. 4. The 32 bits in the validation register may be divided into two groups. One group of 8 contains 1 bit for each of the 8 priority encoders 250–258 which were connected to the holding register 240. These 8 lines are connected to the inputs of another priority encoder 401. The three outputs of this priority encoder 401 contain the address of the most significant priority encoder which was connected to the input together. This is, in fact, the three most significant bits of the address which is required, that is the three most significant bits of the highest numbered detector involved in a coincident event. These three outputs go to three different places. First of all, they form a high group address 420 through which is sent through a fifo (first-in-first-out) 270 to the computer. Secondly, they are presented to an address input of an 8:1 multiplexer 411. The data input of this multiplexer 8:1 which is one of six identified as 410, 411, 412, 413, 414 and 415, is connected to the validation register 262 as are the other multiplexers and provide the other 24 bits to the 32 bit validation register 262. The outputs of these 8:1 multiplexers 410–415 contain the detector address within the group of 8 corresponding to the most significant detector.

At this point all 6 bits of the highest number detector involved in this coincident event have been determined.

The outputs of the priority encoder 401 are also directed to an octal decoder 440 whose function is to regenerate the 8 lines corresponding to the original inputs of the priority encoder 401. Of its outputs only one is true and this is the most significant input to the priority encoder. This is used as a mask, in a high group mask 450–457, to eliminate the most significant input from the inputs to a second priority encoder 402. Since the most significant line has been eliminated from consideration by the second priority encoder 402, its three outputs determine the address of the least significant group of 8 detectors involved in the coincident event. Its outputs are then routed again three ways, similar to the outputs of the first priority encoder 401 and thus the least significant six bits of the address are determined. This process is repeated one more time, in 441, 460–467 and 403, to make sure that only two detectors are involved in each event. Thus we have generated a 12 bit address which can be used to increment a memory location in the computer's memory.

The output address is stored in a first-in-first-out (F1 and F0) register so that the instantaneous speed of the events can be higher than that of the computer input port. This register is loaded with the calculated address and that address is subsequently retrieved when the computer can make use of it.

This memory can be thought of as a square area 64×64 words in size (see FIG. 1) which will always contain the highest number detector on the Y axis (the most significant 6 bits) and the X detector (the least significant 6 bits) along the XX's. It will be observed that because of the priority structure of this data, events will only be collected in an area above a diagonal drawn between the bottom left and top right corners of this square. Since this would be somewhat wasteful of the computer's memory, the coincidence analysis circuit contains a method of complementing the high and low detector address under certain circumstances.

The detector array rotates back and forwards (2.8° the half the angular separation between adjacent detectors) while collecting data. A position encoder generally indicated by 480 in FIG. 2 connected to the detector array is used to switch on either one 280, 282, 284 or another 290, 292, 294 set of buffers which form the output to the computer. The buffer elements which are enabled with the detector array rotated from its normal position 290, 292, 294 complement each bit of the address thus filling in a mirror image of the data set in the bottom right half of the square address space as shown in FIG. 5.

Since the computer may not always be ready to accept events as fast as they are generated by the coincidence analysis circuit, a fifo (first-in-first-out) register which is 16 words deep is used to buffer the data from the address generator to the computer.

Figure 5:
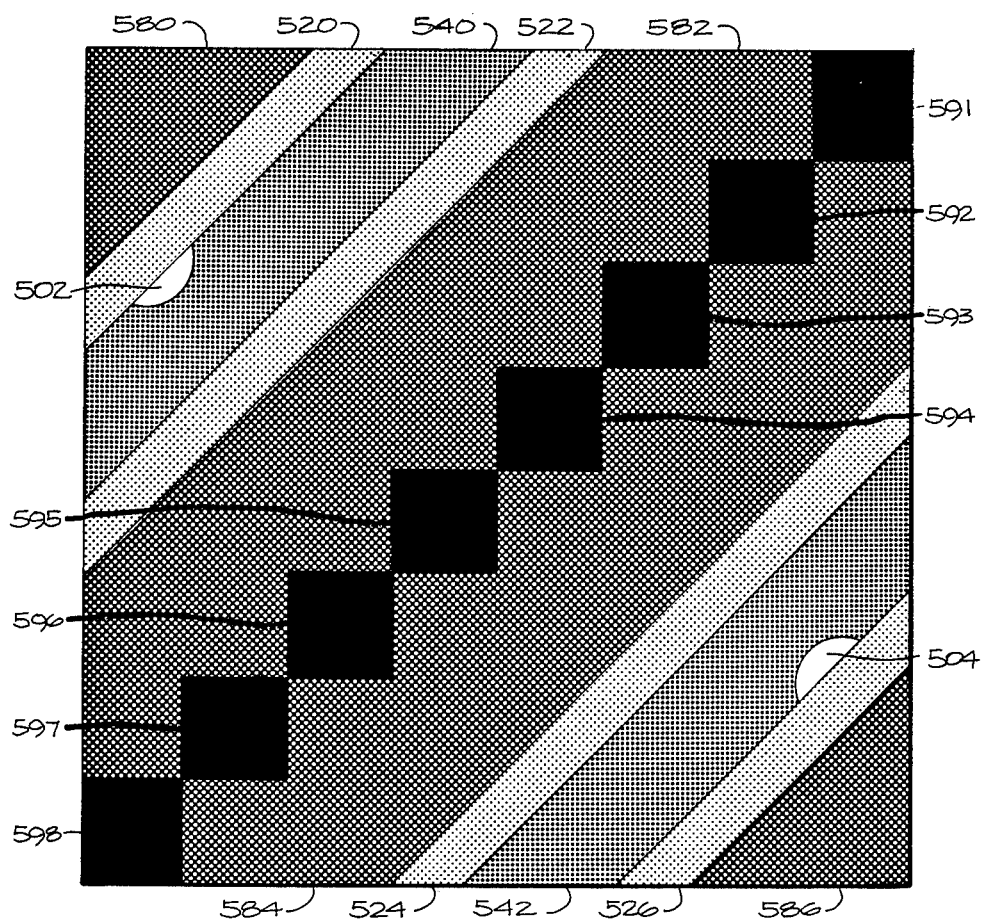

FIG. 5 shows a representation of the "raw data" matrix produced by the circuit from a typical patient scan. The brightest (white) colours correspond to the highest count in a cell of the matrix. The white regions 502, 504 correspond to high count rate from a tumour in the brain. The lines 520, 522, 524, 526 correspond to counts from the skull of the patient. The regions 540, 542 correspond to counts from the brain. The regions 580, 582, 584, 586 correspond to random events between detectors the line between which does not pass through the patient. These events can be used to estimate the random count rate from other detector pairs. The black squares 591–598 contain no data. Detectors corresponding to these areas are both on the same input priority encoder 250, 258. If two such detectors recorded an event simultaneously, the circuit would detect a single event and reject it. This raw data is used to reconstruct an image of a cross section through the head.

ADVANTAGES OF THE INVENTION, MAY BE SUMMERIZED AS FOLLOWS

1. The electronic circuit described is an efficient method of determining that only two detectors in a large array recorded a simultaneous event. All other events are rejected.
2. Only one circuit is required to analyze the events from 64 detectors.
3. An efficient and unique way of determining which 2 detectors were involved in each coincident event has been described.
4. This technique does not require any components which are not available readily commercially at this time.
5. This address generation scheme does not require a read only memory to determine the address eliminating the need for special purpose hardware to be programmed or constructed for this determination.
6. The circuit is designed in such a way to eliminate the most common events (single events) eliminating them from further consideration.
7. Individual stages of the circuit process the data asynchronously allowing the deadtime to be reduced at high counting rates.

What is claimed is:

1. A coincidence detector circuit for receiving a plurality of pulsed input signals, pairs of which occur within a selected coincidence resolving time and require to be identified, said detector circuit comprising:
   (a) input means for receiving pulsed input signals and converting them into level discriminated signals;
   (b) a multiple bit delay to which the level discriminated signals are applied for generating output signals corresponding to and delayed with respect to the level discriminated signals;
   (c) a multiple bit holding register connected to receive the delayed output signals from said multiple bit delay for generating holding register output signals which are the multiple bit delay outputs at the selected coincidence resolving time after the occurrence of any of the pulsed input signals;
   (d) a plurality of priority encoders connected to receive output signals from said holding register, said encoders having a plurality of groups of output signals, each of which contains an address of the most significant input, and a further output signal when one or more input signals are present, and including a parity verification circuit for analyzing the further output signal and applying the groups of output signals and the further output signal as an overall output signal from the plurality of priority encoders when the parity is even;
   (e) a multiple bit validation register receiving the overall output signal from said plurality of priority encoders, said validation register retaining even parity pairs of said pulsed input signals in an encoded form for a predetermined time;
   (f) a high group priority encoder connected to receive output signals from said validation register, for generating an address during the predetermined time, following which the even parity pairs of output signals are received, said priority encoder having outputs which together contain the address of the most significant priority encoder receiving outputs from the holding register;
   (g) a high group decoder connected to receive output signals from said high group priority encoder, said high group decoder regenerating the highest numbered input to said high group priority encoder;
   (h) a high group mask connected to receive the regenerated inputs from said high group decoder, said high group mask eliminating the highest numbered input;
   (i) a low group priority encoder connected to receive output signals from said high group mask and having outputs which together contain the address of a second priority encoder receiving outputs from the holding register, after an appropriate propagation delay;
   (j) a low group decoder connected to receive the address from said low group priority encoder;
   (k) a low group mask connected to receive output signals from said low group decoder and from said high group mask, for generating output signals;
   (l) a further priority encoder, eliminating events in which an even number of detectors other than two respond, connected to receive the output signals from said low group mask; and (m) a plurality of high and low group multiplexers receiving said plurality of groups of output signals from said validation register, said high group multiplexers having output address signals corresponding to the most significant input signals of said plurality of input signals, said low group multiplexers having output address signals corresponding to the least significant group of input signals of said plurality of input signals the outputs from said high group and low group priority encoders and high group and low group multiplexers generating a unique address for both detectors after an appropriate propagation delay.

* * * * *